US012370124B2

(12) United States Patent
Kim et al.

(10) Patent No.: US 12,370,124 B2
(45) Date of Patent: Jul. 29, 2025

(54) MEDICAL NEEDLE

(71) Applicant: WONTECH Co., Ltd., Daejeon (KR)

(72) Inventors: Jong Won Kim, Seongnam-si (KR); Young Seok Seo, Sejong-si (KR)

(73) Assignee: WONTECH CO., LTD., Daejeon (KR)

( * ) Notice: Subject to any disclaimer, the term of this patent is extended or adjusted under 35 U.S.C. 154(b) by 317 days.

(21) Appl. No.: 18/059,375

(22) Filed: Nov. 28, 2022

(65) Prior Publication Data
US 2023/0201078 A1  Jun. 29, 2023

(30) Foreign Application Priority Data

Dec. 27, 2021  (KR) .................. 10-2021-0188888
Jan. 28, 2022  (KR) .................. 10-2022-0012859

(51) Int. Cl.
A61H 39/08  (2006.01)
A61H 39/00  (2006.01)

(52) U.S. Cl.
CPC ......... *A61H 39/086* (2013.01); *A61H 39/002* (2013.01); *A61H 2039/005* (2013.01); *A61H 2201/10* (2013.01); *A61H 2201/5005* (2013.01)

(58) Field of Classification Search
CPC ............... A61H 39/086; A61H 39/002; A61H 2039/005; A61H 2201/10; A61H 2201/5005
See application file for complete search history.

(56) References Cited

U.S. PATENT DOCUMENTS

| 6,306,160 | B1 | 10/2001 | Nidetzky |
| 6,916,329 | B1* | 7/2005 | Zhao .................... A61N 1/0502 606/189 |
| 7,824,394 | B2* | 11/2010 | Manstein ........... A61B 18/1477 606/49 |
| 2013/0110150 | A1* | 5/2013 | Yoo .......................... A61N 1/20 606/189 |
| 2018/0055729 | A1* | 3/2018 | Ding ........................ A61N 1/18 |

FOREIGN PATENT DOCUMENTS

| KR | 10-2013-0042378 | A | | 4/2013 |
| KR | 20150102357 | A | * | 9/2015 |
| KR | 10-1580036 | B1 | | 12/2015 |

OTHER PUBLICATIONS

Extended search report dated Jun. 2, 2025.

* cited by examiner

*Primary Examiner* — Mohamed G Gabr
*Assistant Examiner* — Khoa Tan Le
(74) *Attorney, Agent, or Firm* — Harvest IP Law, LLP

(57) ABSTRACT

Proposed is a medical needle which performs treatment by stimulating acupuncture point of a human body, the medical needle including an electrical stimulation output module which generates a first signal which is an electromagnetic wave, an optical stimulation output module which generates a second signal which is a laser, and a probe needle which is inserted into a skin tissue of a human body to stimulate acupuncture point of the human body and receives the first signal generated from the electrical stimulation output module and the second signal generated from the optical stimulation output module so as to provide the first signal and the second signal to the skin tissue.

9 Claims, 5 Drawing Sheets

MEDICAL NEEDLE

CROSS REFERENCE TO RELATED APPLICATION

The present application claims priority to Korean Patent Application No. 10-2021-0188888, filed on Dec. 27, 2021, and Korean Patent Application No. 10-2022-0012859, filed on Jan. 28, 2022, the entire contents of which are incorporated herein for all purposes by this reference.

BACKGROUND OF THE INVENTION

Field of the Invention

The present disclosure relates generally to a medical needle. More particularly, the present disclosure relates to a medical needle which can irradiate skin tissue with a laser and an electromagnetic wave together.

Description of the Related Art

Recently, as the development of medical technology and the development of new drugs having various complex therapeutic functions are actively progressing, the number of geriatric diseases is increasing while average life span extends and an aging phenomenon continues. In addition, repetitive tendencies of busy work life and leisure activities cause an imbalance in eating habits and lifestyles of the young and old, resulting in damage to health, and need for continuous health management is emerging.

Recently, most patients want non-surgical treatment, and as a result, interest in traditional oriental medicine and oriental medicine treatment is growing, and oriental medicine with a long tradition is growing into a new high value-added industry.

Light therapy treatment, which has recently been actively applied in oriental medicine, is therapy in which a light-based machine or equipment is used to stimulate meridian and facilitate the flow of chi and blood to treat diseases and natural or artificial light is used.

In phototherapy, an ultraviolet ray, a visible ray, an infrared ray, and a laser are mainly used, and it is known that when these rays irradiate an affected area to stimulate the meridian, the meridian is adjusted as a whole to be treated.

Low-level laser therapy (LLLT) among phototherapies used in oriental medicine may be seen as belonging to a treatment which combines acupuncture and warm meridian therapy among treatment categories of oriental medicine. Here, the low-level laser therapy acts to "replenish chi, strengthen the kidney, and warm a door of life" and is a treatment method of using blood collaterals in oriental medicine and may be seen as a method of preventing and treating diseases by stimulating chi and blood distributed in the blood collaterals.

SUMMARY OF THE INVENTION

Accordingly, the present disclosure has been made keeping in mind the above problems occurring in the related art, and the present disclosure is intended to propose a medical needle which can irradiate the skin simultaneously with an electromagnetic wave and a laser through one needle and can prevent a burn on one part of the skin due to a rapid temperature rise thereof caused by an electromagnetic wave and a laser simultaneously irradiating the one part of the skin.

Technical tasks to be achieved by the present disclosure are not limited to the technical tasks mentioned above, and other technical tasks not mentioned will be clearly understood by those skilled in the art from the following description.

In order to achieve the above objectives, according to an embodiment of the present disclosure, there is provided a medical needle which performs treatment by stimulating acupuncture point of a human body, the medical needle including: an electrical stimulation output module which generates a first signal which is an electromagnetic wave; an optical stimulation output module which generates a second signal which is a laser; and a probe needle which is inserted into a skin tissue of a human body to stimulate acupuncture point of the human body and receives the first signal generated from the electrical stimulation output module and the second signal generated from the optical stimulation output module so as to provide the first signal and the second signal to the skin tissue.

In the embodiment of the present disclosure, the medical needle may further include: a first control signal generator which transmits a first control signal for controlling at least one of waveform, frequency, and magnitude of the first signal to the electrical stimulation output when module the electrical stimulation output module and the probe needle are connected to each other; and a second control signal generator which transmits a second control signal for controlling at least one of waveform, frequency, and magnitude of the second signal to the optical stimulation output module when the optical stimulation output module and the probe needle are connected to each other.

In the embodiment of the present disclosure, the electrical stimulation output module may output a first treatment signal, in which at least one of the waveform, frequency, and magnitude of the first signal is controlled according to the first control signal, to the skin tissue with which the probe needle is in contact, and the optical stimulation output module may output a second treatment signal, in which at least one of the waveform, frequency, and magnitude of the second signal is controlled according to the second control signal, to the contacted skin tissue.

In the embodiment of the present disclosure, the probe needle may include: a needle body which has a through hole formed therein and an end of the needle body is formed pointedly in a tapered shape, the needle body being configured to be inserted into the skin tissue of a human body and provide the first treatment signal to the contacted skin tissue; a laser terminal which is located in a portion of the through hole and receives the second treatment signal to provide the second treatment signal to the contacted skin tissue; a connection cable which is connected to the electrical stimulation output module and the optical stimulation output module at a first end thereof and is connected to the needle body and the laser terminal at a second end thereof, the connection cable being configured to transmit the first treatment signal output from the electrical stimulation output module to the needle body, or to transmit the second treatment signal output from the optical stimulation output module to the laser terminal; and a buffer member formed to cover an outer circumferential surface of the needle body.

In the embodiment of the present disclosure, the medical needle may further include: a timer which adjusts a pulse period for each of a plurality of pulse signals when the first control signal or the second control signal is output by having the plurality of pulse signals.

In the embodiment of the present disclosure, when the first control signal and the second control signal are applied to the timer respectively from the first control signal generator and the second control signal generator, the timer may adjust output time of at least one pulse of pulse signals according to the first control signal and output time of at least one pulse of pulse signals according to the second control signal to be different from each other.

According to the embodiment of the present disclosure, the skin can be irradiated simultaneously with an electromagnetic wave and a laser through one needle, and a burn on one part of the skin due to a rapid temperature rise thereof caused by the electromagnetic wave and laser simultaneously irradiating the one part of the skin can be prevented.

The effects of the present disclosure are not limited to the above effects, and should be understood to include all effects that can be inferred from the description of the present disclosure or the configuration of the invention described in the claims.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
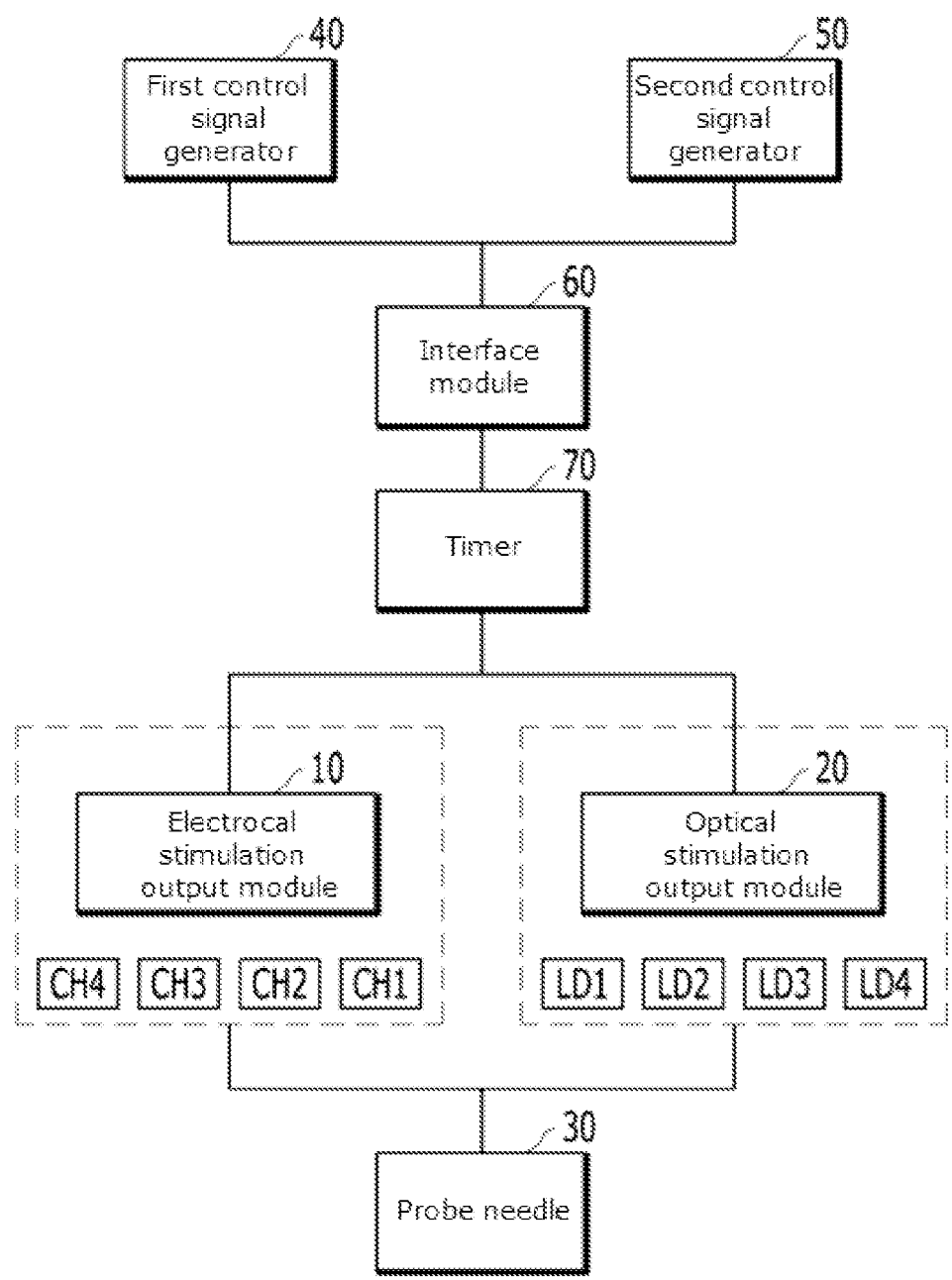
FIG. 1 is a block diagram of roughly illustrating the configuration of a medical needle according to the embodiment of the present disclosure.

Hereinafter, the present disclosure will be described with reference to the accompanying drawings. However, a medical needle of the present disclosure may be implemented in many different forms and thus is not limited to embodiments described herein. And in order to clearly explain the present disclosure, parts irrelevant to the description are omitted in the drawings, and similar reference numerals are attached to similar parts throughout the specification.

Throughout the specification, when a part is said to be "connected (contacted or combined)" with another part, this is includes a case in which the part is not only "directly connected", but also "indirectly connected" with the another part with another member placed therebetween. In addition, when a part "includes" a certain component, it means that the part may further include other components without excluding the other components unless otherwise stated.

Terms used in this specification are only used to describe specific embodiments, and are not intended to limit the present disclosure. Singular expressions include plural expressions unless the context clearly dictates otherwise. In this specification, it should be understood that terms such as "comprises" or "have" are intended to designate that features, numbers, steps, operations, components, parts, or combinations thereof described in the specification exist, but do not preclude the possibility of the existence or addition of one or more other features, numbers, steps, operations, components, parts, or combinations thereof.

Hereinafter, the embodiments of the present disclosure will be described in detail with reference to the accompanying drawings.

FIG. 1 is a block diagram of roughly illustrating the configuration of a medical needle according to the embodiment of the present disclosure.

The medical needle according to the embodiment of the present disclosure may be a medical device which irradiates a skin tissue with a laser and an electromagnetic wave together and stimulates the acupuncture point of a human body so as to treat an affected area. For example, the medical needle of the present disclosure may be a needle for acupuncture.

Referring to FIG. 1, the medical needle according to the embodiment of the present disclosure may include an electrical stimulation output module 10, an optical stimulation output module 20, a probe needle 30, a first control signal generator 40, a second control signal generator 50, an interface module 60, and a timer 70.

The electrical stimulation output module 10 generates a first signal (hereinafter, an electromagnetic wave) which is an electromagnetic wave to be transmitted to a skin tissue. The electrical stimulation output module 10 of the present disclosure may be connected to the probe needle 30 and may apply a generated electromagnetic wave to the probe needle 30. The electrical stimulation output module 10 may have a frequency or pattern in a specific range. According to the embodiment, the electrical stimulation output module 10 may transmit a generated electromagnetic wave to the probe needle 30 in a pulsed manner.

In addition, the optical stimulation output module 20 generates a second signal (hereinafter, a laser), which is a laser, to be transmitted to a skin tissue. The optical stimulation output module 20 may be connected to the probe needle 30 and may apply a generated laser to the probe needle 30.

The optical stimulation output module 20 may generate multiple lasers of a specific wavelength. For example, the optical stimulation output module 20 may generate a laser with a wavelength of 650 nm to 830 nm. Furthermore, the optical stimulation output module 20 may have a frequency or pattern in a specific range. According to the embodiment, the optical stimulation output module 20 may apply a generated laser to the probe needle 30 in a pulsed manner.

As described above, the electrical stimulation output module 10 and the optical stimulation output module 20 of the present disclosure may be configured to output an electromagnetic wave and a laser, respectively, when the probe needle 30 is inserted into a skin tissue.

According to the embodiment of the present disclosure, the probe needle 30 may be inserted into the skin tissue of a human body to stimulate acupuncture point of a human body, and may receive an electromagnetic wave generated by the electrical stimulation output module 10 and a laser generated by the optical stimulation output module 20, and may provide the electromagnetic wave and the laser to the skin tissue of a human body.

The probe needle 30 of the present disclosure may include a plurality of probe needles, and the electrical stimulation output module 10 of the present disclosure may include a plurality of channels CH1, CH2, CH3, and CH4 to correspond to the number of the probe needles 30, respectively. In this case, each of the plurality of channels CH1, CH2, CH3, and CH4 may output an electromagnetic wave having a different frequency domain.

Likewise, the optical stimulation output module 20 of the present disclosure may include a plurality of diodes LD1, LD2, LD3, and LD4 to correspond to the number of the probe needles 30, and each of the plurality of diodes LD1, LD2, LD3, and LD4 may output a laser having a different wavelength within a wavelength band of 650 nm to 830 nm.

According to the embodiment of the present disclosure, the electrical stimulation output module 10 and the optical stimulation output module 20 are coupled to one probe needle 30, and may transmit an electromagnetic wave and a laser through the one probe needle 30 to a skin tissue with which the probe needle 30 is in contact.

In addition, when the electrical stimulation output module 10 and the probe needle 30 are connected to each other, the first control signal generator 40 according to the embodiment of the present disclosure may transmit a first control signal for controlling at least one of the waveform, frequency, and magnitude of a generated electromagnetic wave to the electrical stimulation output module 10.

More specifically, when the end part of the probe needle 30 is inserted into a skin tissue, the first control signal generator 40 may generate the first control signal for transmitting an electromagnetic wave (the first signal) generated from the electrical stimulation output module 10 to a skin tissue. The first control signal is a signal for controlling the electrical stimulation output module 10 to generate an electromagnetic wave (the first signal), and is generated by the first control signal generator 40 to be applied to the electrical stimulation output module 10.

The first control signal generator 40 may apply the first control signal for controlling an electromagnetic wave to be continuously or discontinuously generated and emitted to the electrical stimulation output module 10. For example, the first control signal is a control signal that allows an electromagnetic wave (the first signal) output from the electrical stimulation output module 10 to be output with specific waveform, frequency, and magnitude.

When the electrical stimulation output module 10 includes four channels CH1, CH2, CH3, and CH4 as illustrated in FIG. 1, the first control signal generator 40 according to the embodiment of the present disclosure may transmit the first control signal for controlling electromagnetic waves generated from the electrical stimulation output module 10 and output through the plurality of channels to have a different or same waveform, frequency, and magnitude to the electrical stimulation output module 10.

In addition, the first control signal generator 40 of the present disclosure may determine the connection state of the probe needle 30 and the electrical stimulation output module 10 by checking whether the probe needle 30 is connected to the electrical stimulation output module 10. More specifically, when the electrical stimulation output module 10 and the probe needle 30 are connected to each other, the first control signal generator 40 may receive a connection signal from the electrical stimulation output module 10 connected to the probe needle 30, and may check one connected channel of a plurality of channels constituting the electrical stimulation output module 10 through the received connection signal.

The first control signal generator 40 may check a corresponding channel CH of the electrical stimulation output module 10 connected to the probe needle 30 and may transmit the first control signal to the corresponding channel.

The first control signal described above is a first operation signal for the first signal, and the first signal may be controlled as a first treatment signal (an electromagnetic wave) having waveform, frequency, and magnitude corresponding to the first control signal to be output.

Accordingly, by receiving the first control signal, the electrical stimulation output module 10 of the present disclosure may finally output a first treatment signal in which at least one of the waveform, frequency, and magnitude of an electromagnetic wave (the first signal) is controlled, and may provide the first treatment signal to a skin tissue with which the probe needle 30 is in contact.

When the optical stimulation output module 20 and the probe needle 30 are connected to each other, the second control signal generator 50 may transmit a second control signal for controlling at least one of the waveform, frequency, magnitude of a laser to the optical stimulation output module 20.

More specifically, when the end part of the probe needle 30 is inserted into a skin tissue, the second control signal generator 50 may generate the second control signal for transmitting a laser (the second signal) generated from the optical stimulation output module 20 to a skin tissue. The second control signal is a signal for controlling the optical stimulation output module 20 to generate a laser (the second signal), and is generated by the second control signal generator 50 and is applied to the optical stimulation output module 20.

The second control signal generator 50 may apply the second control signal for controlling a laser to be continuously or discontinuously generated and emitted to the optical stimulation output module 20. For example, the second control signal is a control signal that allows a laser (the second signal) output from the optical stimulation output module 20 to be output with specific waveform, frequency, and magnitude.

When the optical stimulation output module 20 includes four diodes LD1, LD2, LD3, and LD4 as illustrated in FIG. 1, the second control signal generator 50 according to the embodiment of the present disclosure may transmit the second control signal for controlling lasers generated from the optical stimulation output module 20 and output through the plurality of diodes to have a different or same waveform, frequency, and magnitude to the optical stimulation output module 20.

In addition, the second control signal generator 50 of the present disclosure may determine the connection state of the probe needle 30 and the optical stimulation output module 20 by checking whether the probe needle 30 is connected to the optical stimulation output module 20. More specifically, when the optical stimulation output module 20 and the probe needle 30 are connected to each other, the second control signal generator 50 may receive a connection signal from the optical stimulation output module 20 connected to the probe needle 30, and may check one connected one diode of a plurality of diodes constituting the optical stimulation output module 20 through the received connection signal.

The second control signal generator 50 may check a corresponding diode LD of the optical stimulation output module 20 connected to the probe needle 30 and may transmit the second control signal to the corresponding diode.

The second control signal described above is a second operation signal for the second signal, and the second signal is controlled as a second treatment signal (a laser) having waveform, frequency, and magnitude corresponding to the second control signal to be output.

Accordingly, by receiving the second control signal, the optical stimulation output module 20 of the present disclosure may finally output a second treatment signal in which at least one of the waveform, frequency, and magnitude of a laser (the second signal) is controlled and may provide the second treatment signal to a skin tissue with which the probe needle is in contact.

Figure 2:
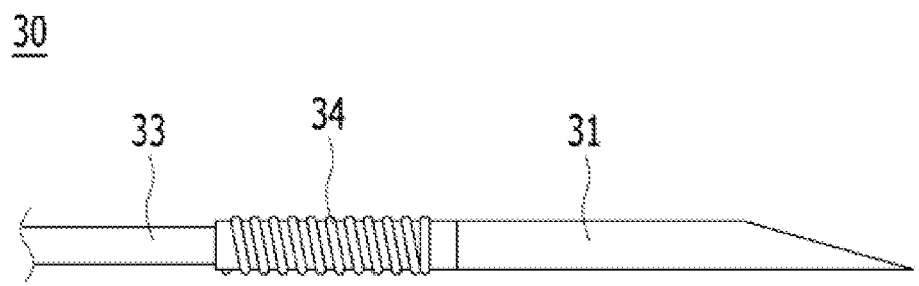
FIG. 2 is a view roughly illustrating a probe needle according to the embodiment of the present disclosure.
Figure 3:
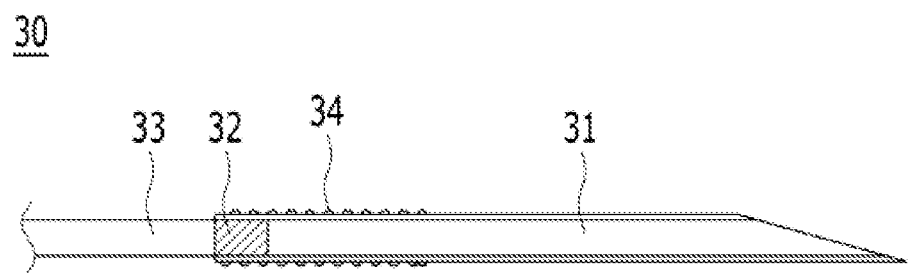
FIG. 3 is a view roughly illustrating the section of the probe needle according to the embodiment of the present disclosure.

FIG. 2 is a view roughly illustrating the probe needle according to the embodiment of the present disclosure, and FIG. 3 is a view roughly illustrating the section of the probe needle according to the embodiment of the present disclosure.

The probe needle 30 according to the embodiment receives an electromagnetic wave (a first treatment signal) and a laser (the second treatment signal) from the electrical stimulation output module 1 and the optical stimulation output module 20, respectively, and is inserted into a human body so as to provide the electromagnetic wave (the first treatment signal) and laser (the second treatment signal), which are received, to the skin tissue with which the probe needle 30 is in contact.

Referring to FIGS. 2 and 3, the probe needle 30 according to the embodiment of the present disclosure may include a needle body 31, a laser terminal 32, a connection cable 33, and a buffer member 34.

The needle body 31 has a through hole formed therein and a first end of the needle body 31 is formed pointedly into a tapered shape, so the needle body 31 may be inserted into the skin tissue of a human body and may provide a received electromagnetic wave to the skin tissue with which the needle body 31 is in contact. The needle body 31 may be provided with the through hole formed therein. When an electromagnetic wave (a first treatment signal) is transmitted to the skin tissue through the needle body 31, heat may be generated in the skin tissue.

The needle body 31 according to the embodiment of the present disclosure, which is a needle for acupuncture defined in oriental medicine, may be inserted into the skin tissue. For example, the needle body 31 may be inserted into an acupuncture point defined in oriental medicine among areas of the skin tissue. In this case, the needle body 31 may have the effect of the needle defined in oriental medicine.

The laser terminal 32 is located in the through hole formed inside the needle body 31, and may receive the second treatment signal output from the optical stimulation output module 20 and may the second treatment signal to the skin tissue with which the needle body 31 is in contact. When a laser is provided to the skin of a human body or the skin tissue by the laser terminal 32 according to the embodiment, heat may be generated in the skin tissue.

The connection cable 33 is connected to the electrical stimulation output module 10 and the optical stimulation output module 20 at a first end thereof and is connected to the needle body 31 and the laser terminal 32 at a second end thereof. The connection cable 33 may transmit the first treatment signal output from the electrical stimulation output module 10 to the needle body 31 or may transmit the second treatment signal output from the optical stimulation output module 20 to the laser terminal 32.

As illustrated in FIGS. 2 and 3, the buffer member 34 may be formed to cover the outer circumferential surface of the needle body 31. The buffer member 34 of the present disclosure serves to enable a user to easily grip the probe needle 30.

Referring back to FIG. 1, the interface module 60 of the present disclosure may monitor whether an electromagnetic wave (a first treatment signal) is emitted to correspond to the first control signal generated by the first control signal generator 40, and may monitor whether a laser (the second treatment signal) is emitted to correspond to the second control signal generated by the second control signal generator 50.

The interface module 60 is connected to each of the electrical stimulation output module 10, the optical stimulation output module 20, the first control signal generator 40, and the second control signal generator 50, and may transmit the first and second control signals to the electrical stimulation output module 10 and the optical stimulation output module 20, respectively, such that the first and second treatment signals corresponding to the first and second control signals are output when the interface module 60 receives the first and second control signals from the first control signal generator 40 and the second control signal generator 50, respectively.

The interface module 60 according to the embodiment of the present disclosure may function to prevent the first and second control signals applied respectively from the first control signal generator 40 and the second control signal generator 50 from being accidentally delivered to the optical stimulation output module 20 and the electrical stimulation output module 10, respectively.

In addition, the interface module 60 may monitor whether the electrical stimulation output module 10 and the optical stimulation output module 20 operate according to each control signal according to the first control signal generator 40 and the second control signal generator 50.

The timer 70 may be connected to the interface module 60 and may adjust the first and second control signals delivered from the interface module 60. The timer 70 of the present disclosure may individually adjust each signal when the timer 70 receives the first and second control signals from the first control signal generator 40 and the second control signal generator 50, respectively, or when the timer 70 receives the first control signal or the second control signal from the first control signal generator 40 or the second control signal generator 50, respectively.

According to the embodiment of the present disclosure, when the first control signal or the second control signal is output by having a plurality of pulse signals, the timer 70 may adjust at least one of a pulse width, a pulse period, and pulse amplitude for each of the plurality of pulse signals.

In the embodiment, when the timer 70 receives the first control signal to be applied to each of multiple channels CH1, CH2, CH3, and CH4 to emit an electromagnetic wave having the same magnitude (energy) until a first time DT1 from predetermined reference time from the first control signal generator 40, the timer 70 may adjust pulse output time of the entirety or any one portion of the first control signal.

More specifically, when the first control signal is transmitted to the timer 70 in the form of multiple pulses, the timer 70 may adjust output time of any one pulse to be adjusted so as to adjust a time interval between the one pulse to be adjusted and a pulse earlier or later in output time than the one pulse to be adjusted.

Figure 4:
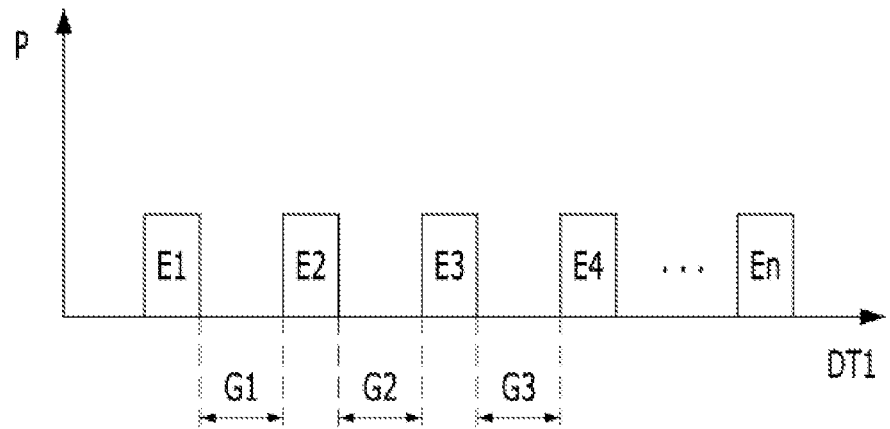
FIG. 4 is a reference diagram illustrating a profile of a signal for transmitting an electromagnetic wave of the medical needle according to the embodiment of the present disclosure.

FIG. 4 is a reference diagram illustrating a profile of a signal for transmitting an electromagnetic wave of the medical needle according to the embodiment of the present disclosure.

Referring to FIG. 4 according to the embodiment of the present disclosure, the first control signal may include a first pulse E1, a second pulse E2, a third pulse E3, a fourth pulse E4, and an Nth pulse En, and when each pulse is output with the same magnitude (energy), the same pulse width, and the same pulse period, the timer 70 may adjust output time of at least one pulse of the multiple pulses such that a time interval between each pulse can be adjusted.

For example, the timer 70 may adjust time at which the first pulse E1 is emitted and the second pulse E2 is output to time later than an existing time according to the first control signal so that an output interval G1 between the first pulse E1 and the second pulse E2 can be increased. Next, the timer 70 may adjust output time of each of the third pulse E3 and the fourth pulse E4 to correspond to the adjusted output time of the second pulse E2 and may adjust a second output interval G2 and a third output interval G3 to have the same intervals.

As described above, the timer 70 may adjust output time of each pulse and may output a first treatment signal of each pulse whose output time is adjusted from the electrical stimulation output module 10.

Figure 5:
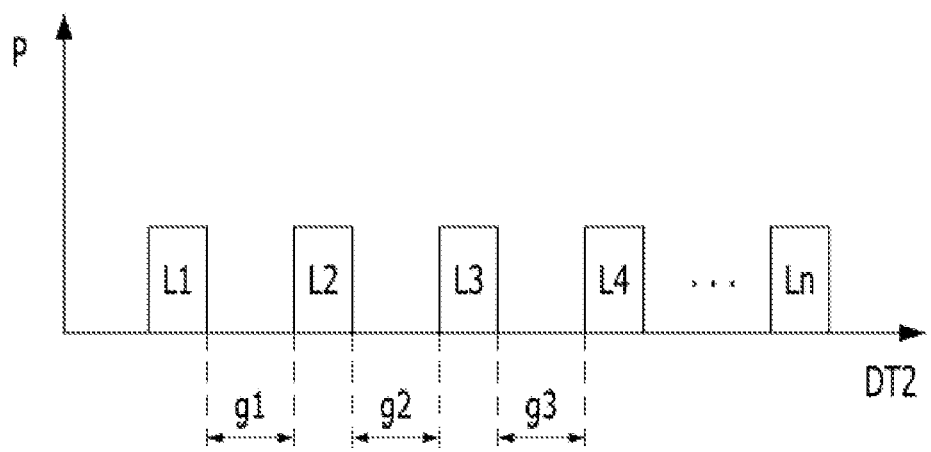
FIG. 5 is a reference diagram illustrating a profile of a signal for transmitting a laser of the medical needle according to the embodiment of the present disclosure.

FIG. 5 is a reference diagram illustrating a profile of a signal for transmitting a laser of the medical needle according to the embodiment of the present disclosure.

According to another embodiment of the present disclosure, when the timer 70 receives the second control signal to be applied to each of multiple diodes LD1, LD2, LD3, and LD4 to emit a laser having the same magnitude (energy) until a second time DT2 from predetermined reference time from the second control signal generator 50, the timer 70 may adjust pulse output time of the entirety or any one portion of the second control signal.

More specifically, when the second control signal is transmitted in the form of multiple pulses, the timer 70 may adjust output time of any one pulse to be adjusted so as to adjust a time interval between the one pulse to be adjusted and a pulse earlier or later in output time than the one pulse to be adjusted.

Referring to FIG. 5 according to the embodiment of the present disclosure, the second control signal includes a first pulse L1, a second pulse L2, a third pulse L3, a fourth pulse L4, and a Nth pulse Ln, and when each pulse is output with the same magnitude (energy), the same pulse width, and the same pulse period, the timer 70 may adjust output time of at least one pulse of the multiple pulses such that a time interval between each pulse can be adjusted.

For example, the timer 70 may adjust time at which the second pulse L2 is output after the emission of the first pulse L1 to time later than an existing time according to the second control signal so that an output interval g1 between the first pulse L1 and the second pulse L2 can be increased. Next, the timer 70 may adjust output time of each of the third pulse L3 and the fourth pulse L4 to correspond to adjusted output time of the second pulse L2, and may adjust the second output interval g2 and the third output interval g3 to have the same intervals.

As described above, the timer 70 may adjust output time of each pulse and may output a second treatment signal of each pulse whose output time is adjusted from the optical stimulation output module 20.

According to still another embodiment of the present disclosure, when the timer 70 receives the first control signal from the first control signal generator 40 together with the second control signal from the second control signal generator 50, the timer 70 may individually adjust output time of each of the first and second control signals.

Figure 6:
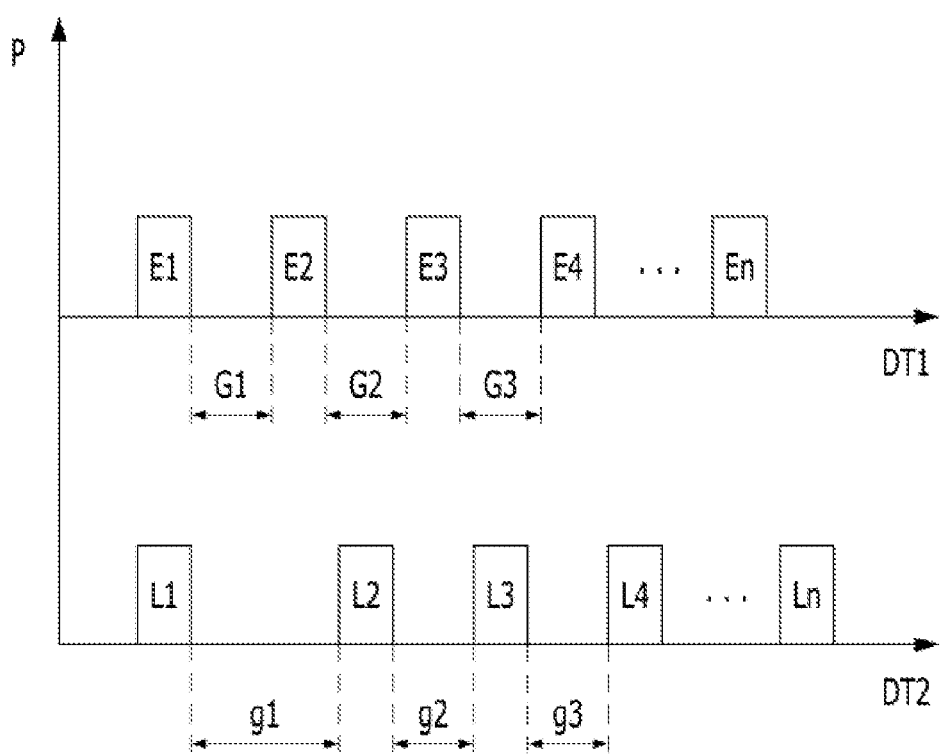
FIG. 6 is a reference diagram illustrating profiles of an electromagnetic wave and a laser whose output time is adjusted by a timer according to another embodiment of the present disclosure.

FIG. 6 is a reference diagram illustrating profiles of an electromagnetic wave and a laser whose output time is adjusted by the timer according to the still another embodiment of the present disclosure.

Referring to FIG. 6, when the first and second control signals for controlling the electrical stimulation output module 10 and the optical stimulation output module 20 to output an electromagnetic wave and a laser together are applied to the timer 70 from both the first and second control signal generators 40 and 50, the timer 70 may adjust output time of the laser in a process in which the electromagnetic wave is output.

Referring to FIG. 6 according to the embodiment, when multiple pulses E1, E2, E3, and E4 constituting the first control signal and multiple pulses L1, L2, L3, and L4 constituting the second control signal are applied to the timer 70 by having the same magnitude (energy), the same pulse periods, and the same pulse widths, the timer 70 may select a pulse whose output time is intended to be adjusted among the multiple pulses according to the first control signal and the second control signal and may adjust the output time of the selected pulse.

For example, when the pulses E1, E2, E3, and E4 according to the first control signal and the pulses L1, L2, L3, and L4 according to the second control signal are applied to the timer 70 by having the same magnitude (energy), the same pulse periods, and the same pulse widths, the timer 70 may adjust output time of the pulses according to the second control signal such that output time of the remaining pulses L2, L3, L4, and Ln except for the first pulse L1 of the second control signal and output time of the pulses E2, E3, E4, and En according to the first control signal are different from each other without overlapping each other. That is, in this case, the first pulse E1 of the first control signal and the first pulse L1 of the second control signal may be output by overlapping each other in output time.

As described above, since output time of each pulse is adjusted by the timer 70, the electrical stimulation output module 10 and the optical stimulation output module 20 may output the first treatment signal and the second treatment signal whose output time is adjusted.

Accordingly, in a process in which the first treatment signal (an electromagnetic wave) and the second treatment signal (a laser) are output respectively from the electrical stimulation output module 10 and the optical stimulation output module 20 and are transmitted through the probe needle 30 to the skin tissue, a burn on one part of the skin due to a rapid temperature rise thereof caused by the electromagnetic wave and the laser simultaneously transmitted to the one part of the skin can be prevented.

Figure 7:
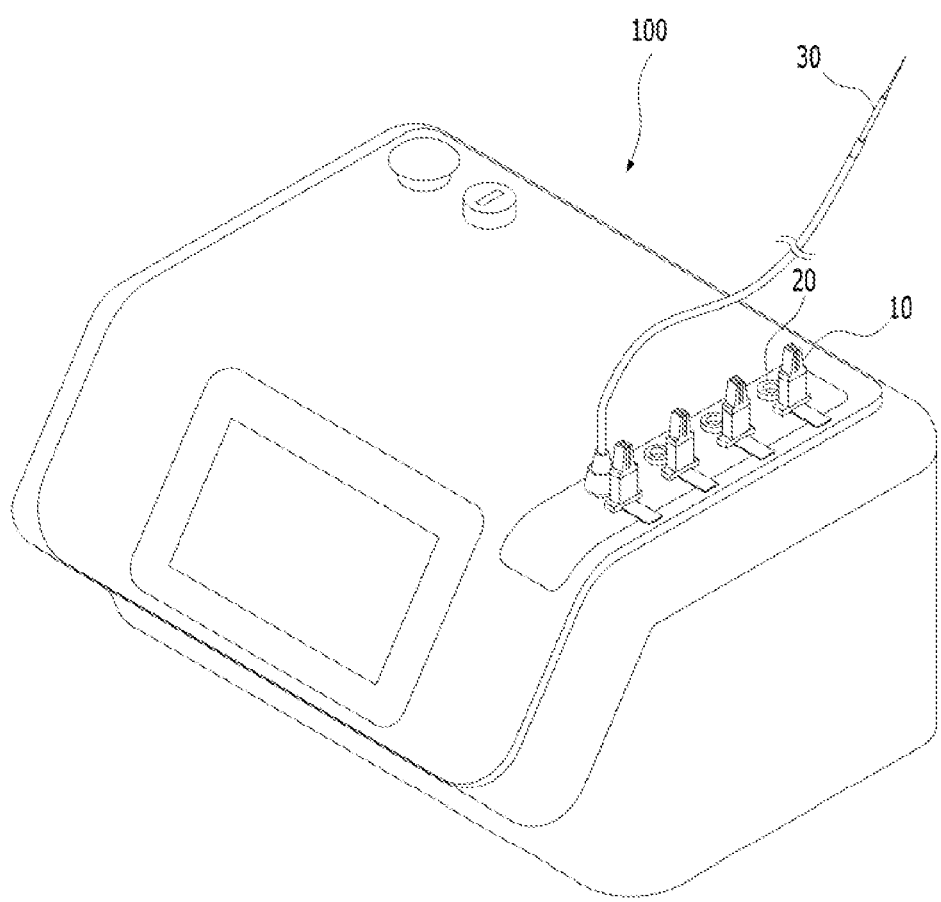
FIG. 7 is a perspective view illustrating the medical needle according to the embodiment of the present disclosure.

FIG. 7 is a perspective view illustrating the medical needle 100 according to the embodiment of the present disclosure. Referring to FIG. 7, the probe needle 30 according to the embodiment of the present disclosure may be used in a state in which the probe needle 30 is coupled to the optical stimulation output module 20. According to the embodiment, the connection cable 33 provided on an end of the probe needle 30 may be fitted into and coupled to the optical stimulation output module 20, and when the connection cable 33 is coupled in this manner, a laser applied from the optical stimulation output module 20 and an electromagnetic wave applied from the electrical stimulation output module 10 may be transmitted to a second end of the needle body inserted into the skin of a human body. After the probe needle 30 is used, the probe needle 30 is preferably stored separately from the optical stimulation output module 20.

The description of the present disclosure described above is for illustrative purposes, and those skilled the art to which the present disclosure belongs will be able to understand that the embodiments can be easily transformed into another specific form without changing the technical spirit or essential characteristics of the present disclosure. Therefore, the embodiments described above should be understood as illustrative in all respects and not limiting. For example, each component described as a single type may be implemented in a distributed manner, and similarly, components described as distributed may be implemented in a combined form.

The scope of the present disclosure is indicated by the following claims, and all changes or modifications derived from the meaning and scope of the claims and equivalent concepts thereof should be construed as being included in the scope of the present disclosure.

What is claimed is:

1. A medical needle which performs treatment by stimulating acupuncture point of a human body, the medical needle comprising:
    an electrical stimulation output module which generates a first signal which is an electromagnetic wave;
    an optical stimulation output module which generates a second signal which is a laser; and
    a probe needle which is inserted into a skin tissue of a human body to stimulate acupuncture point of the human body and receives the first signal generated from the electrical stimulation output module and the second signal generated from the optical stimulation output module so as to provide the first signal and the second signal to the skin tissue;
    a first signal generator configured to transmit a first control signal to the electrical stimulation output module via a timer for controlling the first signal;
    a second signal generator configured to transmit a second control signal to the optical stimulation output module via the timer for controlling the second signal, and
    the timer which adjusts a pulse period for each of a plurality of pulse signals when at least one of the first control signal and the second control signal is output by having the plurality of pulse signals,
    wherein in a case of dual application when both the first control signal and the second control signal are applied to the timer respectively from the first control signal generator and the second control signal generator, the timer adjusts output time of at least one pulse of pulse signals generated according to the first control signal and output time of at least one pulse of pulse signals generated according to the second control signal to be different from each other such that the at least one pulse of the pulse signals generated according to the first control signal and the at least one pulse of the pulse signals generated according to the second control signal are alternately transmitted to the probe needle.

2. The medical needle of claim 1, wherein
    the first control signal generator transmits the first control signal for controlling at least one of waveform, frequency, and magnitude of the first signal to the electrical stimulation output module when the electrical stimulation output module and the probe needle are connected to each other; and
    the second control signal generator transmits the second control signal for controlling at least one of waveform, frequency, and magnitude of the second signal to the optical stimulation output module when the optical stimulation output module and the probe needle are connected to each other.

3. The medical needle of claim 2, wherein the electrical stimulation output module outputs a first treatment signal, in which at least one of the waveform, frequency, and magnitude of the first signal is controlled according to the first control signal, to the skin tissue with which the probe needle is in contact, and
    the optical stimulation output module outputs a second treatment signal, in which at least one of the waveform, frequency, and magnitude of the second signal is controlled according to the second control signal, to the contacted skin tissue.

4. The medical needle of claim 3, wherein the probe needle comprises:
    a needle body which has a through hole formed therein and an end of the needle body is formed pointedly in a tapered shape, the needle body being configured to be inserted into the skin tissue of a human body and provide the first treatment signal to the contacted skin tissue;
    a laser terminal which is located in a portion of the through hole and receives the second treatment signal to provide the second treatment signal to the contacted skin tissue;
    a connection cable which is connected to the electrical stimulation output module and the optical stimulation output module at a first end thereof and is connected to the needle body and the laser terminal at a second end thereof, the connection cable being configured to transmit the first treatment signal output from the electrical stimulation output module to the needle body, or to transmit the second treatment signal output from the optical stimulation output module to the laser terminal; and
    a buffer member formed to cover an outer circumferential surface of the needle body.

5. The medical needle of claim 1, wherein, in the case of dual application, the timer adjusts the output of the at least one pulse of pulse signals generated according to the first control signal and the output of the at least one pulse of pulse signals generated according to the second control signal to not overlap each other.

6. The medical needle of claim 5, wherein, in the case of dual application and when a first electromagnetic pulse generated according to the first control signal and a first laser pulse generated according to the second control signal overlap, the timer delays either of a second electromagnetic pulse which is immediately following the first electromagnetic pulse or a second laser pulse which is immediately following the first laser pulse and keeps an interval of subsequent electromagnetic pulses and an internal of subsequent laser pulses constant while the second electromagnetic pulse and the subsequent electromagnetic pulses do not overlap the second laser pulse and the subsequent laser pulses.

7. The medical needle of claim 1, wherein the electrical stimulation output module comprises a plurality of channels, each of which outputs an electromagnetic wave having a different frequency domain.

8. The medical needle of claim 7, wherein the optical stipulation output module comprises a plurality of diodes, each of which outputs a laser having a different wavelength within a wavelength band of 650 nm to 830 nm.

9. The medical needle of claim 8, wherein the first and second control signal generators
- determine to which one of the plurality of channels and to which one of the plurality of diodes the probe needle is connected, and
- generates the first control signal corresponding to the connected one of the plurality of channels and the second control signal corresponding to the connected one of the plurality of diodes.

* * * * *